United States Patent
Berndt

(10) Patent No.: US 9,316,324 B2
(45) Date of Patent: *Apr. 19, 2016

(54) SHEAR VALVE WITH SILICON CARBIDE MEMBER

(75) Inventor: Manfred Berndt, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 1155 days.

This patent is subject to a terminal disclaimer.

(21) Appl. No.: 12/606,726

(22) Filed: Oct. 27, 2009

(65) Prior Publication Data

US 2010/0101989 A1    Apr. 29, 2010

(30) Foreign Application Priority Data

Oct. 29, 2008  (EP) .................................. 08105690

(51) Int. Cl.
| | |
|---|---|
| *F16K 11/07* | (2006.01) |
| *F16K 11/074* | (2006.01) |
| *F16K 25/00* | (2006.01) |
| *G01N 30/20* | (2006.01) |
| *G01N 35/10* | (2006.01) |
| *B01D 15/16* | (2006.01) |

(52) U.S. Cl.
CPC ............ *F16K 11/074* (2013.01); *F16K 25/005* (2013.01); *G01N 30/20* (2013.01); *G01N 35/1097* (2013.01); *B01D 15/16* (2013.01); *G01N 2030/202* (2013.01); *Y10T 137/86863* (2015.04)

(58) Field of Classification Search
CPC . F16K 11/074; F16K 25/005; G01N 35/1097; G01N 30/20; G01N 2030/202; B01D 15/16; Y10T 137/86863

USPC .............. 210/635, 656, 659, 198.2, 424; 73/61.56; 137/625.46; 251/129.15

See application file for complete search history.

(56) References Cited

U.S. PATENT DOCUMENTS

| | | | | |
|---|---|---|---|---|
| 3,872,889 A | * | 3/1975 | Smith et al. .............. | 137/625.21 |
| 4,068,528 A | | 1/1978 | Gundelfinger | |
| 4,517,938 A | * | 5/1985 | Kruger ..................... | 123/190.17 |
| 4,576,338 A | * | 3/1986 | Klomp ......................... | 239/452 |
| 4,654,052 A | * | 3/1987 | Sharp ................................ | 95/82 |
| 4,994,180 A | * | 2/1991 | Sims et al. .................. | 210/198.2 |
| 5,139,119 A | * | 8/1992 | Karnopp ..................... | 188/266.3 |
| 5,494,258 A | * | 2/1996 | Weissgerber et al. ......... | 251/368 |
| 5,699,885 A | * | 12/1997 | Forster .......................... | 188/317 |
| 5,993,654 A | * | 11/1999 | Black ......................... | 210/198.2 |

(Continued)

FOREIGN PATENT DOCUMENTS

| | | |
|---|---|---|
| EP | 0321774 A2 | 3/1994 |
| EP | 1520837 A1 | 4/2005 |

(Continued)

*Primary Examiner* — Ernest G Therkorn

(57) ABSTRACT

A shear valve, for use in a high performance liquid chromatography system, comprises a first shear valve member and a second shear valve member. At least one of the first and second shear valve members is adapted to be moved with respect to the other. One of the first and second shear valve members comprises a plurality of ports, and the other comprises at least one fluid path for fluidly coupling respective ones of the ports in dependency on a relative movement position of the first and second shear valve members with respect to each other. The first shear valve member is at least partially coated with or comprised of silicon carbide.

17 Claims, 3 Drawing Sheets

(56) References Cited

U.S. PATENT DOCUMENTS

| | | | |
|---|---|---|---|
| 6,358,413 B1* | 3/2002 | Maiefski | 210/198.2 |
| 6,910,394 B2* | 6/2005 | Kriel | 73/863.11 |
| 7,217,359 B2* | 5/2007 | Nakanishi et al. | 210/198.2 |
| 7,341,283 B2* | 3/2008 | Moses et al. | 285/226 |
| 8,297,589 B2* | 10/2012 | Dourdeville et al. | 251/129.19 |
| 8,438,910 B2* | 5/2013 | Berndt | 73/61.56 |
| 2002/0178843 A1* | 12/2002 | Kriel | 73/863.73 |
| 2003/0098076 A1 | 5/2003 | Nichols | |
| 2005/0166708 A1* | 8/2005 | Meier et al. | 75/235 |
| 2007/0068873 A1* | 3/2007 | Oroskar et al. | 210/659 |
| 2007/0251582 A1* | 11/2007 | Farkh et al. | 137/455 |
| 2009/0321356 A1* | 12/2009 | Gerhardt et al. | 210/656 |
| 2010/0012192 A1* | 1/2010 | Dourdeville et al. | 137/1 |
| 2010/0101989 A1* | 4/2010 | Berndt | 210/188 |

FOREIGN PATENT DOCUMENTS

| | | |
|---|---|---|
| WO | 03/074898 A1 | 9/2003 |
| WO | 2006/056236 A1 | 6/2006 |
| WO | PCT/EP07/056735 A1 | 1/2009 |

\* cited by examiner

SHEAR VALVE WITH SILICON CARBIDE MEMBER

This application claims priority from European Patent Application, No. EP 08105690.5 filed on 29 Oct. 2008, which is incorporated by reference in its entirety.

BACKGROUND

The present invention relates to shear valves, in particular in a high performance liquid chromatography application.

In high performance liquid chromatography (HPLC, see e.g. http://en.wikipedia.org/wiki/HPLC), a liquid has to be provided usually at a very controlled flow rate (e. g. in the range of microliters to milliliters per minute) and at high pressure (typically 20-100 MPa, 200-1000 bar, and beyond up to currently 200 MPa, 2000 bar) at which compressibility of the liquid becomes noticeable. For liquid separation in an HPLC system, a mobile phase comprising a sample fluid with compounds to be separated is driven through a stationary phase (such as a chromatographic column), thus separating different compounds of the sample fluid.

Valves are commonly used in HPLC applications, e.g. injection valves for injecting a liquid sample into a high pressure flowing stream of liquid, a purge valves for positive displacement pumps, flow path switching valves, etc. Such valves used in HPLC applications are often multi-position rotary valve. Examples of multi-position rotary valve are disclosed in U.S. Pat. No. 4,068,528 A (two-position valves) or US 2003/0098076 A1 (multi-function rotary valves or random-access, dual, three-way, rotary switching valves).

Shear valves, which can be used in multi-way embodiments, are usually formed by a housing and a body defining a stepped cavity in which the rotor or seal is positioned. The housing contains at least two shear seal valve members positioned to be aligned with ports in the rotor (body) to establish communication between the shear seal means. Shear valves are usually provided as rotary valves (such as the aforementioned rotary valves) or translational valves (often also called sliding valves), such as disclosed in EP 0321774 A2.

A multi-way switching valve provides a means for selectively routing a fluid input flow to the valve to one of more alternate output flows from the valve. A rotary valve is of the type wherein fluid flow is directed by rotating a valve rotor element to discrete angular positions relative to a stationary valve stator element. A dual rotary valve provides two valves in one valve body, both simultaneously operated by the positioning of the valve rotor. Rotary switching valves are commonly used, for example, in HPLC and other analytical methods to selectively direct a flow stream of one or more fluids along alternate paths to an analytical device or containment vessel.

The aforementioned US 2003/0098076 A1 shows in its FIG. 1 a conventional type of dual, three-way, switching valve 220, which includes a disc-shaped rotor with a set of rotor grooves in the front face of the rotor that contacts, in a fluid-tight manner, the face of a cylindrically shaped stator body at a rotor-stator interface. Inlet passages and outlet passages, longitudinally bored through the stator body to the rotor-stator interface, are selectively fluidly coupled through the rotor grooves corresponding to the rotation of the rotor relative to the stator. Pivoting of the rotor enables the rotor grooves to fluidly couple selected passages of the stator, depending on their placement on the rotor and the angular position of the valve rotor. Model 7030 of Rheodyne, L. P. is an example of this type of switching valve.

WO 2006/056236 A1, EP 1520837 A1, and PCT/EP07/056735, all by the same applicant, show other types or embodiments of valves used in HPLC.

In the aforementioned documents, the stator of the valves is typically made of metal, such as stainless steel, and might comprise a stator seal (surfacing towards the rotor) made of a plastic-type material, such as an inert fluoropolymer, which is chemically inert, does not react with either the solvent or samples. In one embodiment of the U.S. Pat. No. 4,068,528 A, both the stator seal and a rotor seal (surfacing towards the stator) are formed of glass reinforced Tefzel with a chemical inertness approximately that of Teflon and glass and of sufficient mechanical strength to withstand high pressure, e.g., 50 MPa (7000 psi).

WO03074898 A1 relates to metal-ceramic composites for tribological uses and defined pairs based on such material. The friction heat generated between both sliding pairs and friction pairs has to be swiftly dissipated in order to maintain a lubricant film or ensure constant coefficients of friction. The document discloses metal-ceramic composites for friction/sliding uses, with basic compositions containing 30 to 75 percent by volume of one or several metallic phases, preferably aluminum and the alloys thereof, and 25 to 70 percent by volume of one or several non-metallic inorganic component/s as ceramic materials, preferably silicon carbide, aluminum oxide, titanium oxide, and silicates.

In modern HPLC with pressures rising up to 100 MPa and beyond, life time of valves becomes critical, in particular for the injection valve, as higher load on the rotor is required, which causes excessive wear.

SUMMARY

It is an object of the invention to provide an improved valve, in particular for high pressure HPLC applications. The object is solved by the independent claim(s). Further embodiments are shown by the dependent claim(s).

According to the present invention, a shear valve for use in an HPLC system comprises a first shear valve member and a second shear valve member. At least one of the first and second shear valve members is adapted to be moved with respect to the other. One of the first and second shear valve members comprises a plurality of ports, and the other comprises at least one fluid path for fluidly coupling respected ones of the ports in dependency on a relative movement position of the first and second shear valve members (with respect to each other).

While valves in HPLC applications are usually made of combinations of harder and softer materials (such as metal rotors and plastic material stator), which have proved—over decades of HPLC developments—an excellent characteristic and long life behavior, it has been found that an entire different material, silicon carbide, revealed a surprising characteristic and unexpected suitability for the quite rough and severe requirements, in particular high pressure but also aggressive solvents, in HPLC. Accordingly, in embodiments of the present invention the first shear valve member is at least partly coded with or comprised of silicon carbide (SiC), and preferably a sintered silicon carbide (SSiC) material.

It has been found that by using SiC for the first shear valve member allows on one hand faster switching cycles (e.g. switching cycles down to 100 ms or less) of the valve and the other hand that the valve can withstand higher pressure applications such as in a range of 100 MPa and even beyond. Due to the relatively high electrical conductivity of SiC, static charging is reduced or even be avoided, thus allowing faster switching and faster switching cycles. Correspondingly, the relatively high thermal conductivity of SiC reduces local heating by the movement between the first and second shear valve members, thus reducing wear and tear and increasing the wear life span. Lower friction typically results in longer lifetime of the valve. Further, reduction of local heating can also reduce softening of the second shear valve member, e.g. in case the second shear valve member is made of a relatively soft material such as a plastic material.

The application of SiC for the first shear valve member thus allows applying higher prestress or pre-load of the shear valve members in order to achieve required sealing (between both shear valve members) even in high pressure applications (i.e. when the liquid in the flow path of the shear valve is under high pressure). Further, SIC is the second hardest material (after diamond) and can be polished with a very smooth low friction surface finish.

It has been shown that, for example, shear valve members made of a solid material of sintered silicon carbide exhibited a low friction coefficient, hardness of about 9.5, electrical conductivity of about $10^3$ Ωm, chemical inertness even at higher temperatures up to 140° C., and a good mechanical stability for the HPLC requirements. Such SSiC shear valve members have even proved to be suitable for preparative HPLC applications using n-hexane as solvent.

SSiC tends to be a brittle material and can usually withstand a high pressure load, but as most brittle materials it might show limitations under torsion and strain. Depending on the load either coating or solid SSiC may be of advantage.

In one embodiment, the shear valve is embodied as a rotary valve, with the first and second shear valve members being rotably moveable with respect to each other. In another embodiment, the shear valve is embodied as a translational valve, such as a slide valve, with the first and second shear valve members being translationally moveable with respect to each other.

The second shear valve member is preferably at least partially coated with or comprised of a material tribologically matching to the first shear valve member material. This can be achieved, e.g. by using one or a mixture of: a polymer material, a polyetheretherketone (PEEK), a PEEK blend T-series material (as compounds of PEEK/PBI and other additions such as PTFE (e.g. 5-40%), molybdenum disulfide $MOS_2$ (e.g. 1-20%), titanium dioxide (e.g. 1-5%), carbon (e.g. 1-50%), nano-particles such as CNT's carbon nanotubes), PEEK/LCP blends (e.g. with similar additions as mentioned above), SSiC, SiC, SSiC derived from a chemical vapor deposition (CVD) coding process (which might require high surface quality and/or application of lubricants such as carbon or $MOS_2$, a blend of PEEK/PBI/PTFE (PBI) stands for polybenzamidazole, and PTFE stands for polytetrafluoroethylene), a blend of PEEK-HT/PBI/Carbon/PTFE, and a blend of PEK-HT/PBI/Carbon/TlO$_2$/PTFE.

In one embodiment, the shear valve further comprises a housing for housing one of the first and second shear valve members, wherein the housing is pre-stressed (pre-loaded) against the housed shear valve member. This allows reducing breakage or fracture stress, which may occur in the housed shear valve member, in particular in case and as more such shear valve member comprises a ceramic material. The housing is preferably attached to the housed shear valve member by using a shrinking process as known in the art.

Preferably, the first shear valve member is the housed shear valve, thus allowing to frame the ceramic or partial ceramic member and reducing tension.

The housing can be made of or comprise a stainless steel, which might be coated with diamond like carbon (DLC), SiC, SSiC, SiC CVD, or any combination thereof.

In one embodiment, the fluid path of this shear valve comprises a groove, which may be made or comprise at least one of an insert, a ceramic insert and a molded ceramic insert.

In one embodiment, one or more of the ports of the shear valve comprise a through hole having an opening fluidly coupling with the fluid path dependent on the moving position.

In one embodiment, wherein the first shear valve member comprises a plurality of ports, the second shear valve member comprises the at least one fluid path for fluidly coupling respective ones of the port independency on a relative movement position of the first and second shear valve member with respect to each other.

In a further embodiment, the second shear valve member is adapted to be moved with respect to the first shear valve member. Preferably, the second shear valve member is provided as rotor or slider moving on the first shear valve member, which is embodied as static member and not moving.

A drive might be provided for moving the shear valve member to be moved. Alternatively or in addition, the shear valve member to be moved might also be moved manually.

A valve control unit, such as an excenter, might be provided for controlling movement of the shear valve member to be moved.

The shear valve is preferably adapted to conduct a liquid in the at least one fluid path at a high pressure at which compressibility of the liquid becomes noticeable, such as pressure in the range of 20-200 MPa, and particularly 50-120 MPa.

The shear valve can be a sample injection valve for injecting a liquid sample into a high pressure flowing stream of liquid, a high pressure purge valve for a positive displacement pump, or a flow path switching valve for switching from one flow path to another flow path.

The shear valve might be embodied in an HPLC sample injector adapted to introduce a sample fluid into a mobile phase. The mobile phase is to be driven by a mobile phase drive through a separation unit for separating compounds of the sample fluid in the mobile phase. A sample loop is provided for receiving the sample fluid. The shear valve is provided for switching the sample loop between the mobile phase drive and the separation unit for introducing the sample fluid into the mobile phase.

Embodiments of the present invention might be embodied based on most conventionally available HPLC systems, such as the Agilent 1200 Series Rapid Resolution LC system or the Agilent 1100 HPLC series (both provided by the applicant Agilent Technologies—see www.agilent.com—which shall be incorporated herein by reference).

One embodiment comprises a pumping apparatus having a piston for reciprocation in a pump working chamber to compress liquid in the pump working chamber to a high pressure at which compressibility of the liquid becomes noticeable.

One embodiment comprises two pumping apparatuses coupled either in a serial or parallel manner. In the serial manner, as disclosed in EP 309596 A1, an outlet of the first pumping apparatus is coupled to an inlet of the second pumping apparatus, and an outlet of the second pumping apparatus provides an outlet of the pump. In the parallel manner, an inlet of the first pumping apparatus is coupled to an inlet of the second pumping apparatus, and an outlet of the first pumping apparatus is coupled to an outlet of the second pumping apparatus, thus providing an outlet of the pump. In either case, a liquid outlet of the first pumping apparatus is phase shifted, preferably essentially 180 degrees, with respect to a liquid outlet of the second pumping apparatus, so that only one pumping apparatus is supplying into the system while the other is intaking liquid (e.g. from the supply), thus allowing to provide a continuous flow at the output. However, it is clear that also both pumping apparatuses might be operated in parallel (i.e. concurrently), at least during certain transitional phases e.g. to provide a smooth(er) transition of the pumping cycles between the pumping apparatuses. The phase shifting might be varied in order to compensate pulsation in the flow of liquid as resulting from the compressibility of the liquid. It is also known to use three piston pumps having about 120 degrees phase shift.

The separating device preferably comprises a chromatographic column (see e.g. http://en.wikipedia.org/wiki/Column_chromatography) providing the stationary phase. The column might be a glass or steel tube (e.g. with a diameter from 50 μm to 5 mm and a length of 1 cm to 1 m) or a microfluidic column (as disclosed e.g. in EP 1577012 or the Agilent 1200 Series HPLC-Chip/MS System provided by the applicant Agilent Technologies, see e.g. http://www.chem.agilent.com/Scripts/PDS.asp?IPage=38308). For example, a slurry can be prepared with a powder of the stationary phase and then poured and pressed into the column. The individual components are retained by the stationary phase differently and separate from each other while they are propagating at different speeds through the column with the eluent. At the end of the column they elute one at a time. During the entire chromatography process the eluent might be also collected in a series of fractions. The stationary phase or adsorbent in column chromatography usually is a solid material. The most common stationary phase for column chromatography is silica gel, followed by alumina. Cellulose powder has often been used in the past. Also possible are ion exchange chromatography, reversed-phase chromatography (RP), affinity chromatography or expanded bed adsorption (EBA). The stationary phases are usually finely ground powders or gels and/or are microporous for an increased surface, though in EBA a fluidized bed is used.

The mobile phase (or eluent) can be either a pure solvent or a mixture of different solvents. It can be chosen e.g. to minimize the retention of the compounds of interest and/or the amount of mobile phase to run the chromatography. The mobile phase can also been chosen so that the different compounds can be separated effectively. The mobile phase might comprise an organic solvent like e.g. methanol or acetonitrile, often diluted with water. For gradient operation water and organic is delivered in separate bottles, from which the gradient pump delivers a programmed blend to the system. Other commonly used solvents may be isopropanol, THF, hexane, ethanol and/or any combination thereof or any combination of these with aforementioned solvents.

The sample fluid might comprise any type of process liquid, natural sample like juice, body fluids like plasma or it may be the result of a reaction like from a fermentation broth.

The pressure in the mobile phase might range from 2-200 MPa (20 to 2000 bar), in particular 10-150 MPa (100 to 1500 bar), and more particular 50-120 MPa (500 to 1200 bar).

The HPLC system might further comprise a sampling unit for introducing the sample fluid into the mobile phase stream, a detector for detecting separated compounds of the sample fluid, a fractionating unit for outputting separated compounds of the sample fluid, or any combination thereof. Further details of HPLC system are disclosed with respect to the Agilent 1200 Series Rapid Resolution LC system or the Agilent 1100 HPLC series, both provided by the applicant Agilent Technologies, under www.agilent.com which shall be in cooperated herein by reference.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in or by the control unit.

BRIEF DESCRIPTION OF DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s).

DETAILED DESCRIPTION

Figure 1:
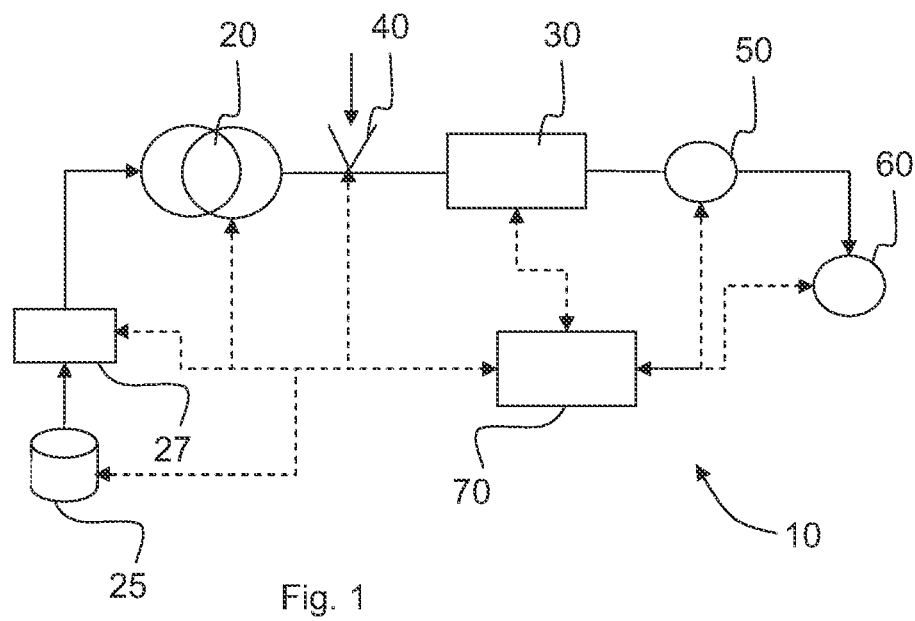
FIG. 1 shows a liquid separation system 10, in accordance with embodiments of the present invention, e.g. used in high performance liquid chromatography (HPLC).

Referring now in greater detail to the drawings, FIG. 1 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 can be provided between the pump 20 and the separating device 30 in order to subject or add (often referred to as sample introduction) a sample fluid into the mobile phase. The stationary phase of the separating device 30 is adapted for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization sample injection with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provides data back.

Figure 2:
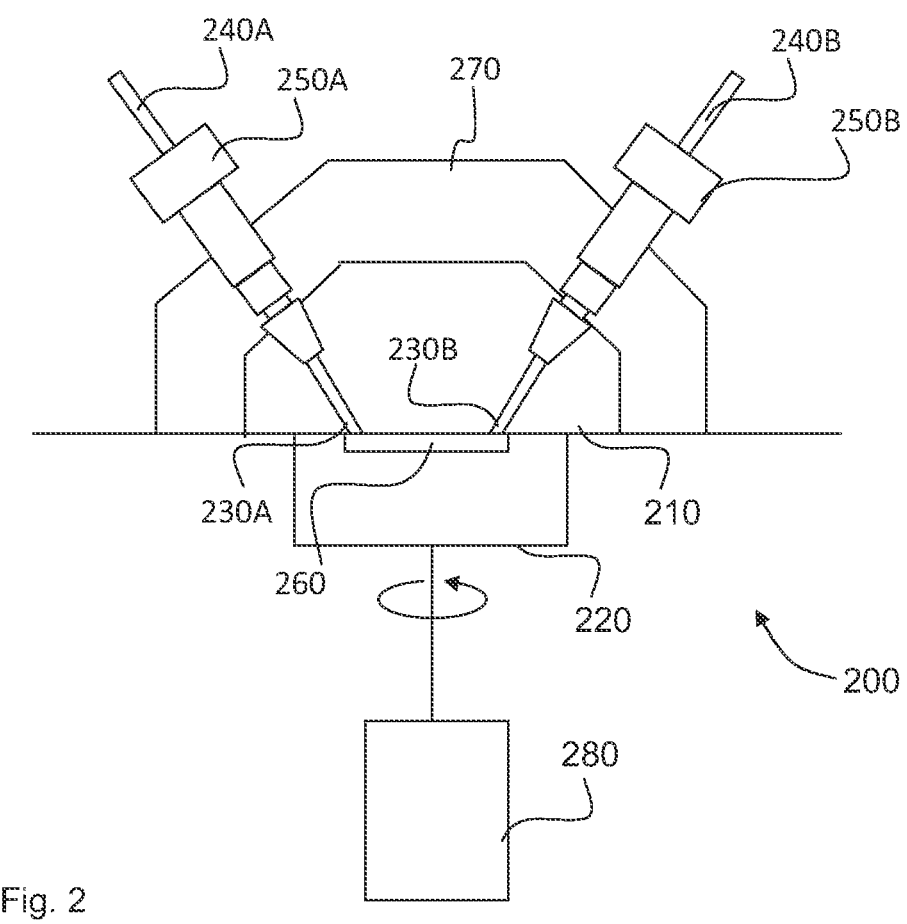
FIG. 2 shows an exemplary embodiment of a shear valve 200 according to the present invention.

FIG. 2 shows an exemplary embodiment of a shear valve 200 according to the present invention, which might be used in the liquid separation system 10 as depicted in FIG. 1. The shear valve 200 comprises a first shear valve member 210 as a stator, and a second shear valve member 220 as a rotor. By rotating the second shear valve member 220, the first and second shear valve members 210 and 220 can be moved with respect to each other. The first shear valve member 210 comprises a plurality of ports 230, with ports 230A and 230B exemplarily shown in FIG. 2. A fluid conduit 240 such as a capillary, e.g. a glass or metal capillary, can be coupled to each port 230 respectively. In FIG. 2, a capillary 240A is coupled via a fitting 250A to the port 230A, and a capillary 240B is coupled via fitting 250B to the port 230B.

The second shear valve member 220 (rotor) comprises a fluid path 260. Dependent on a relative movement position of the first and second shear valve members 210 and 220, the fluid path 260 can be moved to couple between respective ones of the ports 230. In the exemplary illustration of FIG. 2, the fluid path 260 is shown in a position to couple between the ports 230A and 230B, thus allowing a fluid connection between the capillary 240A and 240B. By rotating (as indicated by the curved arrow in FIG. 2) the second shear valve member 220, ports 230A and 230B can be decoupled from each other, thus intermitting the fluid connection between the capillary 240A and 240B. This will also be seen in more detail in FIG. 3.

The rotor of the second shear valve member 220 is preferably moved by a drive 280, such as a motor, but might also be moved (alternatively or in addition) by manual operation. The first shear valve member 210 is at least partly coated with silicon carbide (SiC) or might preferably even be provided by SiC. The material of the second. shear valve member is preferably selected to be tribologically matching to the SiC material of the first shear valve member. In the embodiment of FIG. 2, the first shear valve member 210 is a solid material body of SSiC, while the second shear valve member 220 is embodied by a PEEK Polymer material, or at least the surface towards the first shear valve member 210 is covered therewith.

In the embodiment of FIG. 2, the first shear valve member 210 is housed by a housing 270, which has been fitted to the first shear valve member 210 preferably by using a shrinking process. The housing 270 thus allows pre-stressing against the first shear valve member 210 to reduce tension in the first shear valve member 210. The housing 270 can be made of a stainless steel, which might also be coded with diamond like carbon (DLC).

Figure 3:
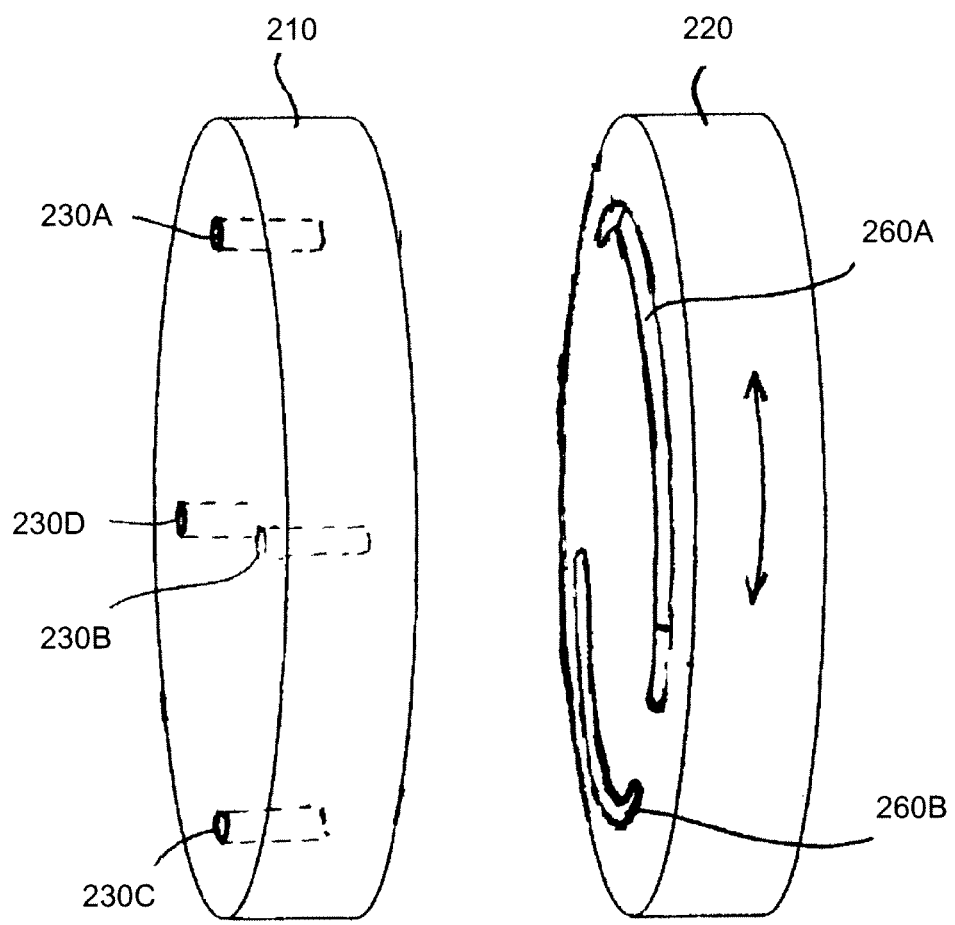
FIG. 3 shows the first and second shear valve members 210 and 220 in a three dimensional view.

FIG. 3 shows the first and second shear valve members 210 and 220 in a three dimensional and enlarged view. In this embodiment, the valve 200 shall be a 2/4 valve, i.e. a valve having two fluid paths 260A and 260B and four ports 230A, 230B, 230c and 230D. By rotating the second shear valve member 220 (as indicated by the arrow), neighboring ones of the ports 230 can be coupled to each other via a respective one of the fluid paths 260A and 260B, as well known in the art and also disclosed by the documents cited in the introductory part of the description.

Figure 4:
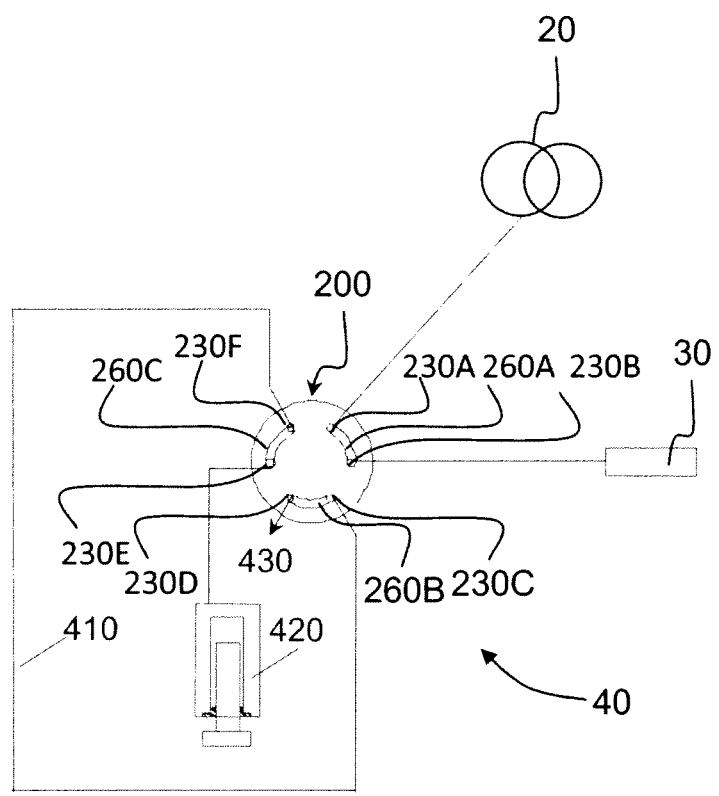
FIG. 4 shows an embodiment of the shear valve 200 in the sample injector 40 of FIG. 1.

FIG. 4 shows an embodiment of the shear valve 200 in the sample injector 40 (see FIG. 1). The shear valve is embodied here as a 3/6 valve, i.e. having three fluid paths and six ports. The injector 40 comprises a sample loop 410, which can be filled via a pump 420 (e.g. a syringe) from any kind of source (e.g. a vessel, vial, bottle, syringe, pump, metering device) generally symbolized here by arrow 430.

The shear valve 200 in the example of FIG. 4 is a 3/6 valve with three fluid paths 260A, 260B and 260C and six ports 230A-230F. In the position as indicated in FIG. 4, the pump 20 is coupled directly via ports 230A and 230B and fluid path 260A to column 30. In this state, the syringe 420 can load sample fluid e.g. from a vessel (symbolized by reference no. 430) into the sample loop 410.

By turning the fluid paths 260A-260C (clockwise or anticlockwise) to the next neighboring port 230, the pump 20 is now coupled via the fluid path 260C and the ports 230A and 230F to the sample loop 410, and again via the fluid path 260A and the ports 230C and 230B to the column 30. In this state the sample loop 410 is now coupled between the pump 20 and the column 30 for injecting any sample fluid contained in the sample loop 410 into the mobile phase, so that compounds of the sample fluid can be separated whilst propagating through the column 30. Rotating the rotor 220 into the (next) neighboring position will lead to the state as shown in FIG. 4.

It is clear that beyond or instead of the shear valve 220 being embodied as a sample injecting valve as shown in FIG. 4, the shear valve 200 may also be used in any other suitable position in the fluid separation system 10 (as depicted in principle in FIG. 1). For example, the shear valve 200 can be provided as a high pressure purge valve for the pump 20, which is usually embodied as a positive displacement pump. Alternatively or in addition, the shear valve 20 might also be used as a flow path switching valve anywhere in the system 10 for switching from one flow path to another flow path, e.g. at a column oven, etc.

The invention claimed is:

1. A shear valve for use in a high performance liquid chromatography system, the shear valve comprising:
    a first shear valve member;
    a second shear valve member; and
    a housing for housing one of the first and the second shear valve members, wherein the housing is shrink-fit to the one of the first and second shear valve members and is prestressed against the housed shear valve member to achieve sealing in pressurized applications,
        wherein at least one of the first and second shear valve members is configured to be moved with respect to the other, one of the first and second shear valve members comprises a plurality of ports, and the other comprises at least one fluid path for fluidly coupling respective ones of the ports in dependency on a relative movement position of the first and second shear valve members with respect to each other,
        wherein the first shear valve member is at least partially coated with or comprised of a ceramic material.

2. The shear valve of claim 1, wherein the ceramic material is a sintered silicon carbide material.

3. The shear valve of claim 1, wherein the shear valve is a rotary valve, and the first and the second shear valve members are rotatably movable with respect to each other.

4. The shear valve of claim 1, wherein the shear valve is a translational valve, and the first and the second shear valve members are translationally movable with respect to each other.

5. The shear valve of claim 1, wherein the second shear valve member is at least partially coated with or comprised of a material tribologically matching to the first shear valve member.

6. The shear valve of claim 1, wherein the second shear valve member is at least partially coated with or comprised of at least one of: a polymer material, polyetheretherketone (PEEK), a blend of PEEK/PBI (polybenzamidazole), PTFE (polytetrafluoroethylene), molybdenum disulfide, titanium dioxide, carbon, and nano-particles, SSiC, SiC, SSiC CVD coated, a blend of PEEK/PBI/PTFE, a blend of PEEK/PBI/Carbon/PTFE, and a blend of PEEK/PBI/Carbon/TlO$_2$/PTFE.

7. The shear valve of claim 1, wherein
the first shear valve member is the housed shear valve member; or
the housing is made of or comprises at least one of: a stainless steel, a DLC coated stainless steel, SiC, SSiC, or SiC CVD coated.

8. The shear valve of claim 1, wherein the fluid path comprises a groove.

9. The shear valve of claim 1, wherein one or more of the ports comprise a through hole having an opening fluidly coupling with the fluid path dependent on the moving position.

10. The shear valve of claim 1, wherein
the first shear valve member comprises the plurality of ports, and
the second shear valve member comprises the at least one fluid path for fluidly coupling respective ones of the ports of the first shear valve member in dependency on a relative movement position of the first and second shear valve members with respect to each other.

11. The shear valve of claim 1, wherein the second shear valve member is configured to be moved with respect to the first shear valve member.

12. The shear valve of claim 1, further comprising at least one of:
a drive for moving the one of the first and second shear valve members to be moved; and
a valve control unit configured to control a movement of the first and second shear valve members with respect to each other.

13. The shear valve of claim 1, wherein
the shear valve is configured to conduct a liquid in the at least one fluid path at a high pressure at which compressibility of the liquid becomes noticeable, or
the shear valve is configured to conduct a liquid in the at least one fluid path at a high pressure in a range of 20-200 MPa, and particularly 50-120 MPa.

14. The shear valve of claim 1, wherein the shear valve is one of:
a sample injection valve for injecting a liquid sample into a high pressure flowing stream of liquid;
a high-pressure purge valve for a positive displacement pump; or
a flow path switching valve for switching from one flow path to another flow path.

15. A sample injector configured to introduce a sample fluid into a mobile phase, wherein the mobile phase is driven by a mobile phase drive through a separation unit for separating compounds of the sample fluid in the mobile phase, the sample injector comprising:
a sample loop for receiving the sample fluid, and
the shear valve of claim 1 for switching the sample loop between the mobile phase drive and the separation unit.

16. A fluid separation system for separating compounds of a sample fluid in a mobile phase, the fluid separation system comprising:
a mobile phase drive configured to drive the mobile phase through the fluid separation system,
separation unit, preferably a chromatographic column, configured to separate compounds of the sample fluid in the mobile phase, and
the shear valve of claim 1 for switching from one flow path to another flow path within a fluid separation flow path between the mobile phase drive and the separation unit.

17. The fluid separation system of claim 16, further comprising at least one of:
a sample injector configured to introduce the sample fluid into the mobile phase;
a detector configured to detect separated compounds of the sample fluid;
a collection unit configured to collect separated compounds of the sample fluid;
a data processing unit configured to process data received from the fluid separation system; or
a degassing apparatus for degassing the mobile phase.

* * * * *